United States Patent
Samain et al.

(10) Patent No.: US 6,759,060 B2
(45) Date of Patent: Jul. 6, 2004

(54) SYNTHETIC PARTICULATE VECTORS AND PREPARATION PROCESS

(75) Inventors: Daniel Samain, Toulouse (FR); Igancio De Miguel, Plaisance Due Touch (FR); Frédérique N'guyen, Toulouse (FR); Pascal Delrieu, Castanet Tolosan (FR); Li Ding, Castanet Tolosan (FR); Nadine Candelotto, Maureville (FR); Corinne Segreto, Sainte Foy Aigrefeuille (FR); Didier Betbeder, Aucamville (FR); Roger Kravtzoff, Fourquevaux (FR); Michel Major, Toulouse (FR)

(73) Assignee: Biovector Therapeutics, S.A., Ramonvillesaint-Agne (FR)

( * ) Notice: Subject to any disclaimer, the term of this patent is extended or adjusted under 35 U.S.C. 154(b) by 0 days.

(21) Appl. No.: 09/112,367

(22) Filed: Jul. 9, 1998

(65) Prior Publication Data

US 2002/0168408 A1 Nov. 14, 2002

Related U.S. Application Data

(63) Continuation-in-part of application No. 08/513,853, filed as application No. PCT/FR94/00228 on Mar. 1, 1994, now Pat. No. 6,013,284.

(30) Foreign Application Priority Data

Mar. 2, 1993 (FR) ............................. 93 02397

(51) Int. Cl.$^7$ ................................. A61K 9/16
(52) U.S. Cl. ....................... 424/498; 428/403
(58) Field of Search ................ 424/405, 484, 424/499, 498; 514/951; 427/2.14, 212; 428/403

(56) References Cited

U.S. PATENT DOCUMENTS

| 4,107,288 | A | * | 8/1978 | Oppenheim et al. |
| 4,501,726 | A | * | 2/1985 | Schroder et al. |
| 5,075,401 | A | * | 12/1991 | Zhang |
| 5,132,285 | A | * | 7/1992 | Tsai |
| 5,151,264 | A | | 9/1992 | Samain |
| 5,188,837 | A | | 2/1993 | Domb |
| 5,705,270 | A | * | 1/1998 | Soon-Shiong et al. |

FOREIGN PATENT DOCUMENTS

| EP | 0277776 | 8/1988 |
| EP | 0344040 | 11/1989 |
| WO | 90/09798 | 9/1990 |
| WO | 91/16068 | 12/1992 |
| WO | 92/21329 | 12/1992 |

OTHER PUBLICATIONS

N. Irving Sax and Richard J. Lewis, Sr., Hawley's Condensed Chemical Dictionary, Eleventh Edition, 1987, Van Norstrand Reinhold, New York, New York, USA.

* cited by examiner

Primary Examiner—Edward J. Webman
(74) Attorney, Agent, or Firm—Burns, Doane, Swecker & Mathis, L.L.P.

(57) ABSTRACT

A synthetic particulate vector comprising a non-liquid hydrophilic nucleus which does not have an external lipid layer grafted thereon. A method for preparing a particulate vector by encapsulating an ionizable active principle, vectors obtainable through said method, and pharmaceutical, cosmetological or food compositions containing such vectors are also disclosed.

8 Claims, No Drawings

SYNTHETIC PARTICULATE VECTORS AND PREPARATION PROCESS

CROSS REFERENCE TO RELATED APPLICATIONS

Which application claims priority under 35 U.S.C. §§119 and/or 365 to PCT/FR94/00228 filed in WIPO on Mar. 1, 1994; and to 93 02397 filed in France on Mar. 2, 1993; the entire content of which is hereby incorporated by reference.

This application is a continuation in part of U.S. application Ser. No. 08/513,853, filed May 1, 1996 now U.S. Pat. No. 6,013,284. Application Ser. No. 08/513,853 is incorporated by reference in its entirety.

BACKGROUND OF THE INVENTION

The present invention relates to new types of particles which can be used alone or as vectors for various compounds. It also relates to a process for the preparation of particulate vectors which makes possible improved control of the active principle charging.

Supramolecular Biovectors or SMBV are particles which are biomimetic of the endogenous vectors of the body and which are capable of encapsulating and of carrying a large number of active principles for, in particular, pharmaceutical, cosmetic or agribusiness use.

A first type of SMBV was described in Application EP 344,040. Their structure is very well suited to the role of vector, in particular as a result of the possibility of modifying their size and their composition according to the molecule or molecules transported and their use.

SMBV are synthesized in three successive steps: synthesis of a central core composed, for example, of crosslinked natural polysaccharide, which can be derived by ionic groups and brought, in particular by ultramilling, to the desired size (between 10 nanometers and a few microns, according to the desired use) establishment of a ring of fatty acids grafted covalently solely at the periphery of the central core, in order to confer a peripheral hydrophobic nature on the latter while retaining its internal hydrophilic nature stabilization of one or of a number of external lipid lamellae, composed in particular of phospholipids or of ceramides, sometimes with the addition of other constituents, for example of constituents of biological membranes.

The active principles, according to their physicochemical characteristics, can be transported either in the external lipid lamellae (in the case of lipophilic or amphiphilic compounds) or within the hydrophilic core (in the case of polar compounds).

Encapsulation of active principles of polar nature can take place, according to the structure of the latter, either before formation of the fatty acid ring or between this step and stabilization of the external lamella.

Despite their suitability for many uses, the synthesis of SMBVs can sometimes cause problems and in particular:

- it requires a step which is problematic to control in grafting the fatty acid ring;
- this grafting, carried out solely at the periphery of the core, must be carried out homogeneously, which requires in particular a prior drying step, under very specific conditions;
- if the active principle is encapsulated before the grafting of the fatty acid ring, some of these molecules, localized, after their encapsulation, at the periphery of the core, can be derived by the fatty acid, leading to modification of the properties of this active principle;
- if the active principle is encapsulated after the grafting of the fatty acid ring, the latter can be detrimental to the penetration of the active principle into the hydrophilic core.

BRIEF SUMMARY OF THE INVENTION

The present inventors have shown that, surprisingly, in certain applications, it was possible to scale down the reaction scheme by not grafting the ring of fatty acids and phospholipids to the periphery of the crosslinked hydrophilic core.

The present inventors have shown that the polysaccharide particles thus obtained could be used as is. They are then named PS-type SMBV, by analogy with supramolecular Biovector or PSC (polysaccharidic core).

The present inventors have indeed shown that the polysaccharide particles, even of small size, could be used provided that suitable charging protocols are adopted.

This is why the subject of the present invention is a synthetic particulate vector, characterized in that it comprises:

a non-liquid hydrophilic core.

A further subject of the present invention is a synthetic particulate vector which consists essentially of a non-liquid hydrophilic core.

DETAILED DESCRIPTION OF THE INVENTION

The notion of vector must, in this instance, be understood within the broad meaning, that is to say that it comprises particles having a support role, for example when they are incorporated in a composition, either as such or for the transportation, the presentation and/or the stabilization of active compounds.

A non-liquid hydrophilic core (or matrix) can be a hydrophilic polymer. The hydrophilic matrix can in particular be composed of polysaccharides or oligosaccharides which are naturally or chemically crosslinked. The polysaccharide is preferably chosen from dextran, starch, cellulose and their derivatives.

The hydrophilic core can be obtained by various methods and in particular, if it is a core of polysaccharide nature, by using a branched or linear biodegradable polysaccharide. This polysaccharide can be, for example, starch or one of its derivatives. Crosslinking processes are known to a person skilled in the art and can be carried out by means of bi- or tri-functional agents, such as epichlorohydrin or phosphorus oxychloride.

The properties of the polysaccharide can be modified by grafting the sugars by acidic or basic ionic functional groups which are important for the encapsulation of ionic active principles.

Encapsulation of the hydrophilic active principles can be carried out at this stage of the synthesis. The gel obtained during the synthetic step is then washed and partially dehydrated by means, for example, of centrifugation techniques, then brought into the presence of the active principle and slowly rehydrated. As the gel has the ability to swell with water, the active principle is carried within the polysaccharide network where it can be bound by ionic bonds with the groups grafted within the gel.

The gel obtained, whether it contains or does not contain an encapsulated compound, must be mechanically ground for the purpose of obtaining particles of desired size. The ultramilling methods are known in the state of the art and can in particular involve a high pressure extrusion using a homogenizer.

Another subject of the present invention is a process for the preparation of a particulate vector, comprising:

a) encapsulating a basic ionizable active principle in a crosslinked hydrophilic matrix grafted by acidic ionic ligands, at a pH below the $pK_a$ of the active principle; and b) increasing the pH of the medium to a value above the $pK_a$ of the active principle.

In fact, the adoption of a suitable protocol for the charging of hydrophilic cores makes it possible to control the topology of the charging.

The hydrophilic matrix is preferably composed of polysaccharides or of oligosaccharides, which are naturally or chemically crosslinked.

This process, which can be used with SMBV, is more particularly important with particles in which the external lipid lamellae have been reduced (L-type SMBV) or eliminated (PS-type SMBV) with respect to the method described above. The present inventors have observed that it is difficult to use such SMBV containing reduced lipid lamellae as vectors for the encapsulation of ionic active principles with conventional charging methods.

In fact, if molecules of the active principle are bound with the polysaccharide particle of the core while being maintained at the periphery of the core, this can result in an instability in the particle suspension, it being possible for the particles to aggregate with one another by virtue of interparticulate bonds due to the active principle. This phenomenon is relatively minor for low levels of charging of active principles, whereas it becomes very important with high levels of charging of active principles. Likewise, the size of the particles is extremely important. With particles of large size (for example, greater than 100 manometers), the ratio of the surface area to the internal volume of the particle is very low; for this reason, in comparison with the total amount of active principle encapsulated, the amount of active principle bound at the periphery of the particles is very low, thus limiting the possibilities of interparticulate bonds. In contrast, when the particles are very small in size, this aggregation phenomenon is very noticeable. It should also be noted that this phenomenon is not very marked with SMBV having a layer of fatty acids grafted onto the core, which then serves to isolate from interparticulate interactions.

In order to overcome this, the present inventors have shown that it is possible to control topologically the penetration of the active principle within the particles by controlling the ionic conditions of the encapsulation.

The polysaccharide cores can be regarded as polyelectrolyte matrices and, as such, they have a pH differential between the inside and the outside of the particle. This phenomenon is due to the more or less significant dissociation of the counterions and to the immobilization of the ionic functional groups on the polysaccharide network. This property makes it possible to control the localization of the active principle to be incorporated, by causing a solely internal encapsulation or an encapsulation solely at the surface or alternatively in the periphery of the core.

When the active principle to be incorporated is basic in nature, its solubilization in a medium with a pH below its pKa leads it to exist in the ionized form; it can then become attached to the anionic groups grafted onto the polysaccharide core. When the pH rises above the pKa, the active principle is in a deionized form, which does not allow it to interact with the matrix. In order to control the localization of the encapsulated active principle, use is therefore made of the pH differential which exists between the inside and the outside of the particle: if the external medium has an excessively high pH, the active principle cannot interact with the ionic groups placed at the periphery of the cores. The internal pH of the cores derived by acidic ligands being lower than the external pH, the active principle, which has entered the particle in the deionized form, becomes ionic again and thus is bound to the anionic groups of the L-type SMBV. In this specific case, the active principle will be localized solely in the core of the particle, to the exclusion of the peripheral region. This type of encapsulation is thus very favorable to an optimum dispersion of the particles.

In the case of acidic active principles, it is possible symmetrically to apply the process with cores derived by basic ligands, according to the following steps:

a) encapsulating an acidic ionizable active principle in a crosslinked hydrophilic matrix grafted by basic ionic ligands, at a pH above the $pK_a$ of the active principle; and b) decreasing the pH of the medium to a value below the $pK_a$ of the active principle.

This type of charging with topological control of the localization of the active principle in the polysaccharide core is particularly advantageous for vectorization applications with SMBV in which the external lipid lamellae have been reduced (L-type SMBV) or eliminated (PS-type SMBV) but it is also suitable and desirable for SMBV already described in the above patents, in order to increase the degree of charging or to minimize the disturbances caused to the structure of the external phospholipid lamella in the case of external attachment of macromolecules, for example of recognition units and in particular of an apoprotein.

Another subject of the invention is a particulate vector composed of a crosslinked hydrophilic core grafted by ionic groups and here called PS-type SMBV. The ionic groups can be anionic groups, such as for example phosphates, succinates or carboxymethylates, or cationic groups, for example quaternary ammoniums or amines. The size of the PS-type SMBV is preferably between 20 and 200 nm.

The crosslinked hydrophilic core can be composed of natural or synthetic polymers which are naturally or chemically crosslinked. Use is in particular made of polysaccharides or oligosaccharides, such as starch, dextran, cellulose and their derivatives.

Advantageously, an active principle is encapsulated in the PS-type SMBV mainly at the center of the matrix; the external part of the core is virtually devoid of active principle, which makes it possible to avoid the aggregation phenomena which generally occur for particles of small size.

One of the subjects of the invention is therefore a particulate vector composed of a crosslinked polysaccharide matrix containing an active principle, the active principle preferably being localized mainly at the center of the matrix.

According to yet another aspect, a subject of the invention is a process for charging which makes it possible to encapsulate the active principle in a complete SMBV, a PS-type SMBV or an L-type SMBV, which can be in the form of a suspension.

The charging is carried out on the particulate vector. In order to do this, the hydrophilic core must contain ionic groups. The process thus requires the following steps:

a) a crosslinked hydrophilic core is prepared in which ionic groups are fixed, b) the active principle is charged within the vector at a pH suitable for the active principle and while supplying energy, c) having incorporated the active principle, the vector is recovered.

In the case of PS-type SMBV, it is difficult to use conventional charging methods for incorporating ionic active principles. It is true that methods with topological control make it possible to overcome this problem. However, topological control requires precise adjustment of the pH which must be compatible with the active principle and the vector.

The present inventors have, therefore, developed an alternative method to overcome these problems. The ionic ligands grafted into the polysaccharide network of the vectors result in a significant affinity for the ionic active principles of opposite charge. However, this affinity, during the incorporation, must be controlled in order to avoid aggregation of the vectors and to make it possible to localize the active principle mainly within the particles. For the precharging, this control requires precise adjustment of the pH or a low level of incorporation. This aggregation is mostly due to localization of the active principle at the surface, which localization is itself due to the presence of ligands at the surface of the particles.

In order to effect this new type of charging, three factors come into play:
   a) a significant affinity of the active principle for the vector in order to provide for incorporation of the active principle: this affinity is created by acidic or basic ionic ligands which are grafted into the crosslinked polymer; the density and the strength of the ligands can be adjusted according to the active principle,
   b) a significant dispersion of the vectors during the incorporation in order to avoid the interactions between particles which promote aggregation: this dispersion can be provided for by the dilution of the vectors in the reaction medium at a concentration which is sufficient to decrease the interparticulate interactions but also at a concentration which is compatible with pharmaceutical applications,
   c) the use of any means for promoting entry of the active principle within the vector: the contribution of energy, in the form, for example, of stirring or of heat, will accelerate the kinetics of entry of the active principle but will also promote dispersion of the vectors; the appropriate form of the active principle, which must be sufficiently ionic to make it possible to attach the active principle but also the least charged, in order to avoid surface interactions.

For SMBV or L-type or PS-type SMBV, it is possible to use incorporation protocols corresponding to these requirements. The presence of grafted ionic ligands in the crosslinked polymer provides for attachment of the active principles for the three species. Dispersion of the vectors can be carried out by suspending PS-type SMBV in water. SMBV or L-type SMBV are prepared from acylated or polysaccharide cores and from phospholipids dispersed beforehand in aqueous medium and are thus suspended in water. The contribution of energy, for example, in the form of stirring or of heat, does not damage the SMBV. It is possible to vary the pHs and to define pH ranges which are compatible with this type of charging.

This new process makes it possible to prepare SMBV of any type which are charged with active principle, while retaining the size of the base vectors. This process thus has many advantages. This method comprises preparing the blank vectors, without active principle, before the incorporation. This makes it possible to process the blank vectors according to conditions which are suitable for the vectors and which do not depend on the active principle to be encapsulated. The vectors are subsequently charged. These conditions can, therefore, be more or less drastic. They also make it possible to be able to characterize the blank vector as a base entity.

Incorporating the active principle in the final step of the process results in the active principle, which is capable of being toxic and expensive, being handled during only one step of the process. This process thus reduces the handlings and the possible losses of the active principle. It, therefore, makes it possible to be more certain as regards safety, but also more profitable.

In addition, for some active principles, the incorporation conditions can be relatively simple, which makes it possible to envision charging the vectors with the active principle at the time of use. This method of preparation at the time of use can eliminate the problems of storage in the liquid state.

This new method of charging is based on the significant affinity between the vectors and the ionic active principles, but also on the simple control of the incorporation by the dispersion of the vectors and the ionic form of the active principle. It has very worthwhile advantages: preparation of the blank vector independent of the active principle, handling of the active principle in a single step and the possibility of preparation at the time of use.

The particulate vectors according to the invention preferably have a diameter of between 10 nm and 5 $\mu$m and more preferably between 20 and 70 nm.

These particulate vectors are intended to carry or to present at their surface one or a number of molecules possessing biological activity. Mention must be made, among these molecules, without this list being limiting, of:
   antibiotics and antivirals,
   proteins, proteoglycans, peptides,
   polysaccharides, lipopolysaccharides,
   antibodies,
   antigens,
   insecticides and fungicides,
   compounds which act on the cardiovascular system,
   anticancers,
   antimalarials,
   antiasthmatics,
   compounds having an effect on the skin,
   constituents of dairy fat globules.

In the examples below, a description will be given of the charging of various products according to their characteristics, and in particular:
   a hydrophilic product of small size intended for systemic administration,
   an active principle possessing anticancer activity,
   two enzymes possessing antibacterial activity, lactoperoxidase and glucose oxidase, and
   a plant extract composed of procyanidol oligomers possessing an antioxidant activity,
   constituents of the fat globule of milk.

The present invention, therefore, provides a pharmaceutical composition, comprising a particulate vector according to the invention and a pharmaceutically acceptable support for its administration. The vectors according to the invention are in particular useful for therapeutic and immunological applications.

The present invention also provides a cosmetological composition comprising a particulate vector as described above, and cosmetologically acceptable excipients.

Finally, food compositions comprising particulate vectors according to the invention form parts of the invention.

The examples which follow are intended to illustrate the invention without limiting the scope thereof.

EXAMPLE 1

Preparation of Polysaccharide Particles with a Mean Diameter of 20 Nanometers, by Twofold Crosslinking of Dextran by Phosphorus Oxychloride 100 g of dextran (Roquette) are introduced into a 3 liter jacketed reactor and are dissolved in 350 ml of demineralized water and 100 ml of 10N sodium hydroxide.

After homogenization, 35.3 ml of $POCl_3$ and 225 ml of 10N sodium hydroxide are added simultaneously.

After the end of the addition of the reactants, the reaction mixture is stirred for a further 15 minutes and then neutralized by addition of hydrochloric acid.

The gel is diluted in 2 liters of demineralized water and homogenized at 900 bars using a high pressure homogenizer (Westfalia). This step makes it possible to obtain matrices with a mean diameter of 20.

The matrices are then washed by precipitation with ethanol in order to remove the salts and then dried by lyophilization at a concentration of 30 g/l of matrices and 20 g/l of ammonium bicarbonate. 75 g of lyophilized matrices are recovered (reaction yield 75%).

EXAMPLE 2

Preparation of Polysaccharide Matrices Grafted by Cationic Quaternary Ammonium Groups 200 grams of amylopectin (Roquette, Lille, Fr.) are dispersed in 500 milliliters of 2N sodium hydroxide in a 5 liter reactor. When the solution is well homogenized, 93.6 grams of glycidyltrimethylammonium chloride (Fluka, CH), corresponding to 0.5 equivalents/ glucose residue, dissolved in 150 milliliters of water, and 11.4 grams (i.e. 9.7 milliliters) of epichloroydrin (Fluka, CH), corresponding to 0.1 equivalents/glucose residue, are simultaneously introduced. The mixture is homogenized for 1 to 2 hours and then left standing for 8 hours. The polymerized starch preparation is then brought to pH 6 by addition of acetic acid. The gel obtained is then washed a number of times with distilled water until all the salts and reaction by-products have been removed. After lyophilization, 244 grams of crosslinked gel are obtained, i.e. a reaction yield of 80%.

EXAMPLE 3

Preparation of Polysaccharide Matrices Grafted by Anionic Groups of Carboxymethyl Type ("CM-Type")

200 grams of dextran (Roquette) are dissolved in 300 milliliters of 7N sodium hydroxide in a 5 liter reactor. When the solution is well homogenized, 9.6 milliliters of epichloroydrin (Fluka, CH), corresponding to 0.1 equivalents/ glucose residue, and 117.2 grams of chloroacetic acid, dissolved in 80 milliliters of water, are simultaneously introduced.

After stirring for 1 hour, 9.6 milliliters of epichlorohydrin and 150 milliliters of 2N sodium hydroxide are added while stirring vigorously. After the end of the addition, the preparation is homogenized for 6 hours and then left standing overnight. The gel thus obtained is suspended in 1 liter of water and acidified to pH 3–4 by addition of 2N hydrochloric acid. The gel is then filtered and washed with distilled water. After lyophilization, 276 grams of gel of carboxymethyl type are obtained, i.e. a yield greater than 80%.

EXAMPLE 4

Preparation of Hydrophilic Matrices, with a Mean Diameter of 1 $\mu$m, by Crosslinking of Starch by Phosphorus Oxychloride 100 g of wheat starch (Roquette) are introduced into a 3 liter jacketed reactor and dissolved in 375 ml of distilled water and 100 ml of 10N sodium hydroxide.

The mixture is stirred for 15 minutes at room temperature.

Once the mixture is homogenized, 11 ml of $POCl_3$ and 50 ml of 10N sodium hydroxide are simultaneously added. After the end of the addition of the reactants, the reaction mixture is stirred for a further 15 minutes and then neutralized to pH 7 by addition of acetic acid.

The gel is washed in a centrifuge (Rousselet) for 30 minutes with distilled water so as to remove the excess salts and reaction by-products.

The gel thus obtained is then homogenized at high pressure (500 bars, Westfalia minilab homogenizer). This step makes it possible to obtain matrices with a mean size of 1 $\mu$m. The titration of 1 g of crosslinked gel using an automatic titrimeter (Methrom 682 titroprocessor) reveals a degree of crosslinking of 0.3 meq of phosphodiester functional groups per gram of crosslinked gel.

PS-type SMBV with a diameter of 1 $\mu$m are thus obtained.

EXAMPLE 5

Production of Ionic Polysaccharide Particles of 200 Nanometers 15 grams of gel obtained according to Example 2, or of CM-type gel obtained according to Example 3, are dispersed in 500 milliliters of distilled water and homogenized by means of a Rannie MiniLab 12-51 homogenizer (APV Rannie, Copenhagen, Dk). The homogenization pressure applied is 600 bars for 12 minutes.

A fluid suspension of basic or acidic crosslinked polysaccharide particles is obtained, the size of the particles, measured with a Coulter N4MD Nanosizer, being centered around 200 manometers. The nanoparticles are then dried by lyophilization in the presence of 20 grams/liter of ammonium bicarbonate.

PS-type SMBV with a diameter of 200 nm are thus obtained, which can be used as is or converted to L-type SMBV.

EXAMPLE 6

Preparation of Anionic Polysaccharide Cores (PSC)

500 g of maltodextrin (Glucidex, Roquette, Lestrem, France) are poured in a 10 liter reactor (TRIMIX) along with 2 liters of demineralized water. After solubilization at 4° C., 500 ml of sodium hydroxide (NaOH) 10M are added with mechanical stirring. When the temperature of the solution has stabilized at 4° C., 1700 ml of 10M NaOH and 283.3 ml of $POCL_3$ are added under controlled flow conditions. The cross linking reaction takes place with mechanical stirring during a 20 hour period. At the end of the 20 hour period, the reacting mixture is stirred an additional 15 minutes. A volume of 5 liters of demineralized water is added and the pH is adjusted to 7.0 by neutralization with glacial acetic acid. The hydrogel obtained is ground under high-pressure. At the end of this step, the mean diameter of the particles is approximately 60 nm. Further purification proceeds as follows:

(i) microfiltration at 0.45 μm to eliminate larger particles,
(ii) diafiltration at constant volume to eliminate smaller molecules (salts, fragments of polysaccharaides, etc). The anionic polysaccharide cores (PSC) are then concentrated, added to sterile flasks, and stored at ~20° C.

EXAMPLE 7

Preparation of Cationic Polysaccharide Cores (PSC)

500 mg of maltodextrine (Glucidex, Roquette, Lestrem, France) are solubilized with 0.880 liters of water at 20° C., with stirring, in a thermoregulated reactor. Seven grams of $NaBH_4$ are added and mixed for 1 hour. 220 ml of NaOH 10 M are added, followed by 30.25 ml of epichlorydrin (Fulka). After 12 hours of reaction, 382.3 g of glycidyltrimethylammonium chloride (Fulka) are introduced and the mixture is stirred for 10 hours. The resulting gel is diluted with 8 liters of demineralized water and the pH is adjusted to 7.0 by neutralization with glacial acetic acid. The hydrogel obtained is ground under high-pressure. The pressure used is 400 bars. At the end of this step, the mean diameter of the particles is approximately 60 nm. Further purification proceeds as follows: (i) microfiltration at 0.45 μm to eliminate larger particles, (ii) diafiltration at constant volume to eliminate smaller molecules (salts, fragments of polysaccharides). The cationic PSC are then concentrated, sampled in sterile flasks and stored at ~20° C.

EXAMPLE 8

Loading of ddCTP in Cationic Polysaccharidic Core (PSC)

Cationic PSC, obtained according to Example 7, is conjugated to an antiviral agent: dideoxy cytidine triphosphate (ddCTP). A water solution of ddCTP (5 mg/ml) is slowly added to the solution of cationic PSC (5.5 mg/ml). Mixing is done at room temperature under magnetic stirring. The ratio of ddCTP/PSC is 10% (weight/weight) with a final concentration of PSC of 5 mg/ml. The preparation is incubated 2 hours at room temperature with magnetic stirring. Free ddCTP is separated from PSC associated ddCTP by ultrafiltration on Amicon device (100 kDa). All ddCTP concentrations are measured by spectrophotometric assays.

The following table provides an example of the association of ddCTP with cationic PSC. A quantitative association is obtained between ddCTP and cationic PSC (yield=98%). This can be explained by the important affinity of the phosphate groups carried by the active principle and the cationic charge carried by the PSC. These associations can be generalized to all nucleosidic antiviral or nucleosidic anticancer compounds under triphosphate form. Moreover, the excellent filterability of the ddCTP/PSC clearly demonstrates the absence of aggregation phenomena during the incorporation process.

| Association of ddCTP and cationic PSC | | |
|---|---|---|
| | PSC | Free |
| Entrapment yield % | 98.2 ± 0.3 | 0 |
| Filtration yield % | 971 ± 0.5 | 99.4 ± 0.8 |

EXAMPLE 9

Loading of hGRF in Anionic Polysaccharidic Cores (PSC)

Anionic PSC are obtained according to Example 6. hGRF (Synthetic human growth hormone releasing factor (1-29)-NH2) in solution in distilled water (6 mg/ml) is introduced drop by drop under ultrasonics in the anionic PSC solution (1.1 mg/ml) (charge 1.7 mEq/g). Solution is left 15 min under ultrasonics, then 4 hours at room temperature. hGRF associated to PSC is separated from free hGRF by ultrafiltration on Microsep (Filtron 300 Kda). hGRF concentration is then measured by UV spectrometry in the ultrafiltration supernatants.

In order to evaluate the incorporation stability, 0.9 ml of PSC-hGRF is mixed with 0.1 ml of PBS* (concentrated 10 times), then incubated 18 hours at 37°. hGRF associated to NPS is separated from free hGRF by ultrafiltration on Microsep (Filtron 300 Kda). hGRF concentration is then measured by UV spectrometry in ultrafiltration supernatants.
* PBS Composition: 10 mM $Na_2HPO_4/NaH_2PO_4$, 120 mMNaCl & 2.7 mM KCl The following table gives results obtained with a PBC concentration of 1 mg/ml and initial ratio hGRF/NPC of 60%. Under these conditions, association between hGRF and PSC is quantitive with incorporation yields higher than 90%. Furthermore, as shown by the stability obtained in PBS, the association hGRF and PSC is stable in physiologic medium.

The following table gives results obtained with a PSC concentration of 1 mg/ml and an initial ratio hGRF/NPC of 60%. Under these conditions, association between hGRF and PSC is quantitative with incorporation yields higher than 90%. Furthermore, as shown by the stability obtained in PBS, the association hGRF and PSC is stable in physiologic medium.

| Incorporation of hGRF in PSC | | | | |
|---|---|---|---|---|
| | hGRF alone | | hGRF WITH PSC | |
| | Average | SD | Average | SD |
| Incorporation yield (%) | 4.9 | 3.5 | 92.6 | 2.5 |
| Incorporation ratio hGRF/PSC (%) | — | — | 55.5 | 4.9 |
| Loss in PBS (%) | — | — | 6.5 | 2.1 |

EXAMPLE 10

Loading of Insulin in Cationic Polysaccharidic Cores (PSC)

500 mg insulin (human recombinant insulin zinc salt) are solubilized in 15.5 ml HCl (0.02M), then neutralized to pH 8.0 with NaOH solution (0.1 M). A solution of cationic PSC (22 g/l) (charge 1.8 mEq/g) obtained according to Example 7 is slowly added to the insulin solution. The preparation obtained by this method is sterilized by filtration on 0.2 μm filters. It can be used for nasal administration after introduction in a spray. Insulin associated to PSC is separated from free insulin by Centricon (100 kDa) ultrafiltration after 1/10 dilution in PBS (1 mM Na2HPO$_4$/NaH$_2$PO$_4$, 12 mM NaCl & 0.27 mM KCl). Insulin concentration is then measured by HPLC in ultrafiltration supernatants.

The following table gives results obtained for the preparation of a clinical batch. With quantitative (100%) association yields, the obtained results show the excellent affinity of insulin for the cationic PSC structure. In these conditions, the obtained preparations are introduced in monospray (Pfeiffer), allowing the delivery of 100 μl, corresponding to a therapeutic dose of 56.6 IU insulin with 2 mg of PSC for an administration volume of 100 μl in each nostril.

|  | PSC |
| --- | --- |
| Association yield | 100% |
| PSC Concentration g/l | 9.6 ± 0.2 |
| Insulin concentration IU/ml | 285 ± 4 |
| Delivered volume (μl) | 93 ± 5 |

EXAMPLE 11

Incorporation of an Enzyme, Lactoperoxidase (LP), in PS-Type SMBV

Lactoperoxidase (LP) is an antibacterial enzyme. It is a basic protein having an isoelectric point of 9.6 and an average molecular weight of approximately 80,000 daltons. 0.5 gram of anionic (CM) PS-type SMBV, obtained according to Example 3 and then 5, is suspended in 100 milliliters of a buffer adjusted to pH 7, below the pI of LP, in a 250 ml round-bottomed flask. 0.5 g of LP (BioSerae), dissolved in 1 milliliter of water, is then introduced with stirring.

The mixture is stirred overnight in a refrigerator (4° C.). The pH is then adjusted to 9.8, above the pI of LP, and incubated for 30 min. The pH is then brought back to 7 and the suspension is then lyophilized in the presence of ammonium bicarbonate (20 grams/liter). PS-type SMBV charged with LP are obtained with a charging yield of 99% and a degree of incorporation of 99% with respect to the weight of the cores, from quantitative determination by LTV at 412 nm.

EXAMPLE 12

Antibacterial Activity of the LP Encapsulated in PS-Type SMBV

Antibacterial Activity Against a Strain of *Escherichia coli:*

An LB glucose culture medium, mixed with a gelose agar, is prepared and poured into antibiogram dishes. The strain of *E. coli* is inoculated at the surface of the gelose at the rate of 200 μl/dish. Sterile paper disks are impregnated with suspensions of encapsulated or nonencapsulated enzymes and deposited on the gelose of the inoculated dishes. The dishes are left to incubate for 24 h at 37° C. and the inhibition diameters around the disks are measured.

The disks were impregnated with enzyme concentrations varying from 0.05 to 0.6 mg/ml of LP. The inhibition diameters vary from 12 to 20 mm and are comparable, whether or not the enzyme has been encapsulated.

EXAMPLE 13

Stabilization of the Antibacterial Activity of Enzyme Encapsulated in PS-Type SMBV A 0.1 mg/ml aqueous lactoperoxidase solution and a suspension of LP encapsulated in PS-type SMBV prepared according to Example 11 and in which the LP concentration is also 0.1 mg/ml is prepared.

These two suspensions are left at 4° C. and quantitatively determined every week and then every month by the method described in Example 12. The activity of the LP solution decreases with time and, after 90 days, the residual activity is no more than 35% of that of the initial activity. In contrast, the activity of the suspension of LP encapsulated in PS-type SMBV stays constant and remains equal to 100% of the initial activity after 90 days.

EXAMPLE 14

Incorporation of an Anticancer Antibiotic, Doxorubicin, in PS-Type SMBV by Using the Method of Charging by Topological Control Doxorubicin is an anticancer antibiotic belonging to the anthracycline family. It is an amphiphilic product characterized by a polyaromatic aglycone, conferring characteristic fluorescence properties on the molecule, and by an amino sugar, daunosamine. The molecular weight of the hydrochloride is 580 and its pKa is 8.5.

Polysaccharide cores prepared as above are used.

1. Incorporation of Doxorubicin without Topological Control

Doxorubicin (0.1 g) in aqueous solution is added progressively to the polysaccharide cores (0.5 g) with magnetic stirring. The suspension obtained is then left stirring for 17 h at room temperature and with the light excluded.

The polysaccharide cores thus charged with doxorubicin have completely precipitated. Even in the presence of detergent and of phospholipids, they cannot be correctly dispersed with a size of 20 nm.

The incorporation of doxorubicin without topological control leads to a complete aggregation of the polysaccharide cores and cannot be used for forming L-type SMBV of 20 nm.

2. Incorporation of Doxorubicin with Topological Control

Doxorubicin (0.1 g) in aqueous solution is added progressively to the polysaccharide cores (0.5 g) with magnetic stirring. The pH is adjusted to 7, below the pKa of doxorubicin, during the addition. The suspension obtained is stirred for 17 h at room temperature and with the light excluded. The pH is then adjusted to 9, above the pKa of doxorubicin, and incubated for 30 min.

After the incubation step at pH 9, the suspension obtained is diluted in 1 l of water and brought to pH 7. The cores thus charged are analyzed: filtration through 0.2 μm of the suspension exhibits a yield of doxorubicin of greater than 95%, which indicates that the size of the polysaccharide cores is 20 nm, and centrifugal ultrafiltration of an aliquot of the suspension demonstrates the absence of free doxorubicin. The results indicate the presence of 4 mg of doxorubicin in the ultrafiltrate and of 46 mg of doxorubicin in the polysaccharide cores, which corresponds to a yield of 92% and a degree of encapsulation of 18% of doxorubicin. Filtration through 0.2 gm of the suspension obtained exhibits a yield of greater than 95%, which indicates that the size of the SMBVs is 20 nm.

EXAMPLE 15

Comparison Between the Incorporation of Doxorubicin in PS-Type SMBV and SMBV

Doxorubicin is an anticancer antibiotic belonging to the anthracycline family. It is an amphiphilic product characterized by a polyaromatic aglycone, conferring characteristic fluorescence properties on the molecule, and by an amino sugar, daunosamine. The molecular weight of the hydrochloride is 580 and its pKa is 8.2–8.5.

Incorporation of Doxorubicin in Polysaccharide Cores

The polysaccharide cores used were crosslinked and functionalized by $POCl_3$ and have a size of 20 nm. Their ionic density is 1.59 mequiv PO4/g.

The polysaccharide cores (10 mg) are dispersed in water (10 ml) under ultrasound. The pH of the cores suspension is adjusted to 7 with 0.1N NaOH. The doxorubicin (4.6 mg), as a 5 mg/ml solution in water, is slowly added while sonicating in 20 μl portions. The pH is adjusted to 7, if necessary, with 0.1N NAOH.

The polysaccharide cores thus charged are characterized by their ability to be filtered through 0.2 μm. The filtration yield is determined by the ratio of the concentrations before and after filtration. After incorporation, 100 μl of the suspension of charged polysaccharide cores are withdrawn in order to determine the doxorubicin concentration. The remainder of the suspension is filtered through a membrane with a porosity of 0.2 μm. A 100 μl aliquot is again withdrawn for the quantitative determination of the doxorubicin. The doxorubicin is quantitatively determined by HPLC after release of the polysaccharide cores.

$$\text{Filtration yield through } 0.2\,\mu m(\%) = \frac{\text{doxorubicin concentration after filtration}}{\text{doxorubicin concentration before filtration}} \times 100$$

the nonincorporated fraction which is determined by centrifugal ultrafiltration. After filtration, 1 ml of the suspension of polysaccharide cores, diluted to 1/2, is deposited on the centrifugal ultrafiltration system (Microsep) and then centrifuged at 7500 g for 30 min. The ultrafiltrate obtained is quantitatively determined by HPLC for doxorubicin.

$$\text{Nonincorporated fraction}(\%) = \frac{\text{doxorubicin concentration in the ultrafiltrate}}{\text{doxorubicin concentration after filtration}} \times 100$$

The filtration yield is 97% and the nonincorporated fraction is less than 5%, leading to an incorporation yield of 99%.

Comparison of the Behavior Under Physiological Conditions of Doxorubicin Incorporated in Polysaccharide Cores and in SMBV The particles which are postcharged in doxorubicin, polysaccharide cores or SMBV, are incubated in PBS at 37° C. at a doxorubicin concentration of 50 μg/ml. At time 0 h and 4 h, 1 ml of the particle suspension is withdrawn and ultrafiltered by centrifuging (7500 g, 30 min) on a Microsep in order to determine the doxorubicin fraction released. The ultrafiltrate obtained is then quantitatively determined for doxorubicin by HPLC. The results are presented in the following table:

| % of doxorubicin remaining incorporated | Type of particles PS-Type SMBV | Type of particles SMBV |
| --- | --- | --- |
| time 0 h | 67 +/− 1 | 62 +/− 1 |
| time 4 h | 64 +/− 3 | 55 +/− 5 |

Behavior Under Physiological Conditions of Polysaccharide Cores and of SMBV which Have Incorporated Doxorubicin by Postcharging The results obtained indicate a difference in behavior of doxorubicin incorporated in these two types of particles: doxorubicin remains incorporated more strongly in the polysaccharide cores than in the SMBV.

The descriptions of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to best explain the principles of the invention and its practical application to enable thereby others skilled in the art to best utilize the invention in various embodiments and with various modifications as are suited to the particular use contemplated. It is intended that the scope of the invention be defined by the claims appended hereto. All references cited herein are incorporated by reference.

What is claimed is:

1. A synthetic particulate vector comprising a non-liquid hydrophilic core which comprises a matrix of polysaccharides or oligosaccharides which are naturally or chemically crosslinked, said hydrophilic core having ionic ligands grafted thereon, wherein said vector does not have an external lipid layer grafted thereon, and further comprising an active principle;

wherein the vector has a diameter of between 10 nm and 5 μm and wherein the polysaccharides or oligosaccharides are cross-linked by means of bi- or tri-functional agents.

2. The synthetic particulate vector according to claim 1, wherein the active principle is an ionizable molecule localized into the matrix.

3. The synthetic particulate vector according to claim 1, wherein said active principle is selected from the group consisting of antibiotics, antiviral agents, proteins, proteoglycans, peptides, poly saccharides, lipopolysaccharides, antibodies, antigens, insecticides, fungicides, compounds which act on the cardiovascular system, anticancer agents, antimalarial agents, antiasthmatic agents, and compounds having an effect on the skin.

4. A synthetic particulate vector consisting essentially of a non-liquid hydrophilic matrix and an active principle wherein said hydrophilic matrix comprises polysaccharides or oligosaccharides which are naturally or chemically crosslinked, said hydrophilic matrix having ionic ligands grafted thereon;

wherein the vector has a diameter of between 10 nm and 5 μm and wherein the polysaccharides or oligosaccharides are cross-linked by means of bi- or tri-functional agents.

5. The synthetic particulate vector according to claim 4, wherein the active principle is an ionizable molecule localized into the matrix.

6. The synthetic particulate vector according to claim 4, wherein said active principle is selected from the group consisting of antibiotics, antiviral agents, proteins, proteoglycans, peptides, polysaccharides, lipopolysaccharides, antibodies, antigens, insecticides, fungicides, compounds which act on the cardiovascular system, anticancer agents, antimalarial agents, antiasthmatic agents, and compounds having an effect on the skin.

7. A synthetic particulate vector consisting essentially of a non-liquid hydrophilic matrix and an active principle wherein said hydrophylic matrix comprises a polyhydroxylated polymer which is naturally or chemically crosslinked, said hydrophilic matrix having ionic ligands grafted thereon;

wherein the vector has a diameter of between 10 nm and 5 $\mu$m and wherein the polymer is cross-linked by means of bi- or tri-functional agents.

8. A synthetic particulate vector comprising a non-liquid hydrophilic core which comprises a matrix of polysaccharides or oligosaccharides which are naturally or chemically cross-linked, said hydrophilic core having ionic ligands grafted thereon, and said vector further comprises an active principal, wherein said vector does not have an external lipid layer grafter thereon;

wherein the vector has a diameter of between 10 nm and 5 $\mu$m and wherein the polysacchanides or oligosaccharides are cross-linked by means of bi- or tri-functional agents.

* * * * *